United States Patent [19]

Bopp et al.

[11] Patent Number: 4,981,474
[45] Date of Patent: Jan. 1, 1991

[54] BODY FLUID DRAINAGE DEVICE

[75] Inventors: Jeffrey S. Bopp, Mundelein; James W. Voegele, Dundee; George J. Stanczak, Chicago, all of Ill.

[73] Assignee: Baxter Travenol Laboratories, Inc., Deerfield, Ill.

[21] Appl. No.: 155,895

[22] Filed: Feb. 16, 1988

[51] Int. Cl.$^5$ .......................................... A61M 37/00
[52] U.S. Cl. .................................. 604/133; 604/119; 604/319; 128/767
[58] Field of Search ...................... 128/765, 767, 760; 604/132, 133, 118, 119, 280, 315, 317, 319–321; 417/472, 234

[56] References Cited

U.S. PATENT DOCUMENTS

| | | | |
|---|---|---|---|
| 3,120,192 | 2/1964 | Winchell | 417/472 |
| 3,818,806 | 6/1974 | Fumagalli | 417/472 |
| 4,429,693 | 2/1984 | Blake et al. | 604/119 |
| 4,583,972 | 4/1986 | Hunter, III | 604/133 |

Primary Examiner—Jerome L. Kruter
Attorney, Agent, or Firm—Mary J. Schnurr; Bradford R. L. Price; Paul C. Flattery

[57] ABSTRACT

A body fluid drainage device that includes a wedge-shaped reservoir evacuator which has a first sidewall and a second sidewall integrally formed and joined along a coextending common edge. A third collapsible bellows-shaped sidewall extends between the nonjoined edges and is sealed to the nonjoined edges of the first sidewall and second sidewall to enclose and form a fluid tight reservoir between the first, second and third sidewalls. An inlet port and outlet port are provided in fluid communication with the reservoir. A one-way valve is provided in the inlet port for permitting fluid flow into the reservoir but preventing fluid flow out of the inlet port. A spring element is provided for storing energy to force the first sidewall away from the second sidewall following compression of the first sidewall towards the second sidewall such that as the first sidewall moves away from the second sidewall a partial vacuum is created within the reservoir for drawing fluid into the reservoir.

10 Claims, 2 Drawing Sheets

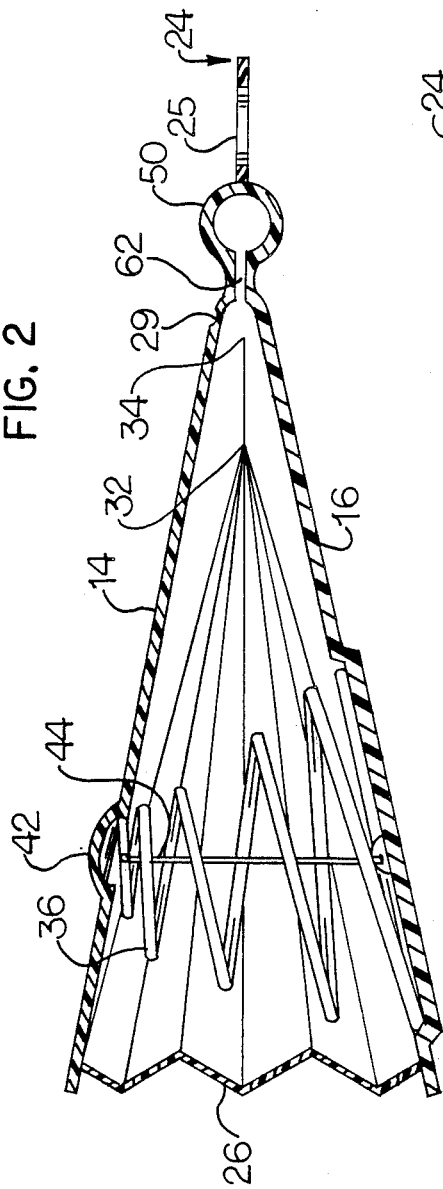
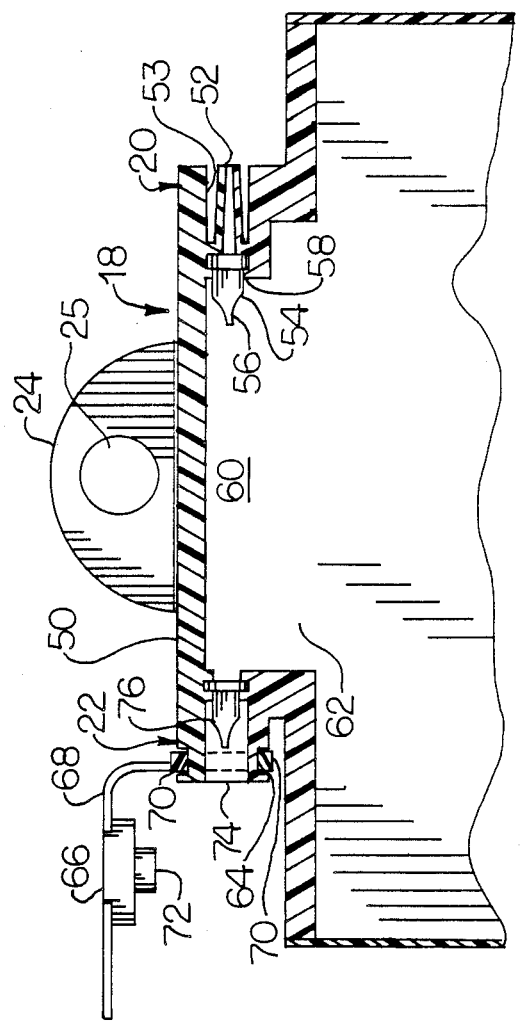
FIG. 2
FIG. 3

BODY FLUID DRAINAGE DEVICE

BACKGROUND OF THE INVENTION

The invention herein relates to the field of drainage systems utilizing vacuum creating devices for withdrawing or draining fluids from body cavities. The invention herein relates to a disposable body fluid drainage device which has particular application for draining exudate from wounds, such as surgically created wounds. Wound drainage reservoirs and body fluid drainage devices are used to remove fluids from surgically created wounds, such as those created in orthopedic surgery, plastic surgery, vasectomies, thoracic and abdominal surgeries.

U.S. Pat. No. 3,875,941 discloses a system for evacuating fluids from the body. The evacuation system therein includes a bellows-type bottle which acts as a reservoir for receiving and collecting the body fluids. The bellows-type bottle is collapsed and as it returns to its initial state it collects fluid. As additional fluid is collected the weight of the fluid extends the bellows bottle thereby creating additional partial vacuum to draw additional fluid into the bottle.

U.S. Pat. No. 4,642,088 discloses a bellows-type apparatus for receiving and reinfusing blood from a patient. The device therein can be initially collapsed, and as it recovers to its original state a partial vacuum is created which can draw blood into the reservoir created within the device.

U.S. Pat. No. 4,429,693 shows a spring-loaded surgical fluid evacuator. The device therein can be initially collapsed against a spring, as the device seeks to recover its original shape by the force of the spring, fluid is drawn into the reservoir.

There are also commercial wound drainage products on the market which consist of a spring loaded cylindrical structure. The end walls of the devices which are parallel plates are held apart by a series of metallic springs, and the cylindrical sidewall joining the end walls is collapsible. Initially the devices are compressed to place tension on the springs. As the springs then push the end walls apart, a partial vacuum is created such that fluid can be drawn into the reservoir created within the devices.

A disadvantage of the present day systems is that they generally require a two-hand operation. That is, in order to compress the devices, two hands are required to initially collapse the devices. The present day systems are also difficult to drain, as the outlet ports are provided in positions where it is difficult to evacuate fluid from the reservoir.

It would be desirable to provide a body fluid drainage device which could be activated by a one-hand operation, which would be easy to use in collecting fluid and in subsequently evacuating the fluid once it is collected. It would also be desirable to provide a device which is compact in size but can readily hold a relatively large volume of fluid. It would also be desirable to create such a device that could be readily carried on a person and which would provide a uniform vacuum to circle a constant evacuation force for evacuating fluid from the patient's body.

SUMMARY OF THE INVENTION

The invention herein is directed to a body fluid drainage device and, in particular, a body fluid drainage reservoir which can provide, upon activation, a partial vacuum within the reservoir for drawing fluid from a patient's body into the reservoir.

The reservoir is generally wedge-shaped and formed by two generally flat sidewalls joined along a coextending common edge. The joining of the two sidewalls creates a living hinge between the two sidewalls. The living hinge can be located on one or both of the sidewalls for controlled bending. Connecting the two sidewalls along their noncoextending and noncommon edges is a third sidewall. The third sidewall forms a fluid tight seal with the first sidewall and the second sidewall. The third sidewall has a pleated structure so that it can collapse as the first and second sidewalls are compressed towards one another. The first sidewall, second sidewall and third sidewall enclose and form the reservoir for the body fluid drainage device.

The body fluid drainage device also includes a spring element which tends to cause the first sidewall and second sidewall to spring apart to its original configuration after the first sidewall and second sidewall have been compressed towards one another. The spring element of the reservoir can be provided by the joining of the first sidewall to the second sidewall, as well as the combination of such a juncture with the pleats of the third sidewall. The spring element can also be provided by a spring or series of springs within the reservoir itself. Such springs can be attached to the first sidewall and second sidewall or merely captured between the first and second sidewalls. By providing springs within the reservoir, a consistent evacuation pressure can be provided within the reservoir among various reservoirs. That is, a relatively constant rate of return of the two sidewalls to their original configuration can be provided.

Also provided on the body fluid drainage device is an inlet port which is in fluid communication with the reservoir. The inlet port is designed to be connectable to tubing, such as a catheter, which leads to the patient from which fluid is to be drained. A one-way valve in the inlet port permits fluid to flow into the body fluid drainage device, but prevents retrograde flow out of the inlet port.

An outlet port is provided on the body fluid drainage device. The outlet port can be provided with a stopper, cap and/or one-way valve to keep it closed until it is desired that fluid be poured from the reservoir. Both the inlet port and outlet port can be provided in a cylindrical housing that is attached to the coextending, common edges of the first sidewall and second sidewall.

BRIEF DESCRIPTION OF THE DRAWINGS

The above-described features and advantages of the body fluid drainage device herein will be described with regard to the following detailed description and the accompanying drawings wherein:

FIG. 2 is a cross-sectional view of the embodiment shown in FIG. 1 taken along lines 2—2;

FIG. 3 is a partial plan view of the body fluid drainage device herein in partial cross-section, illustrating the cylindrical housing for the inlet and outlet ports.

DETAILED DESCRIPTION

Figure 1:
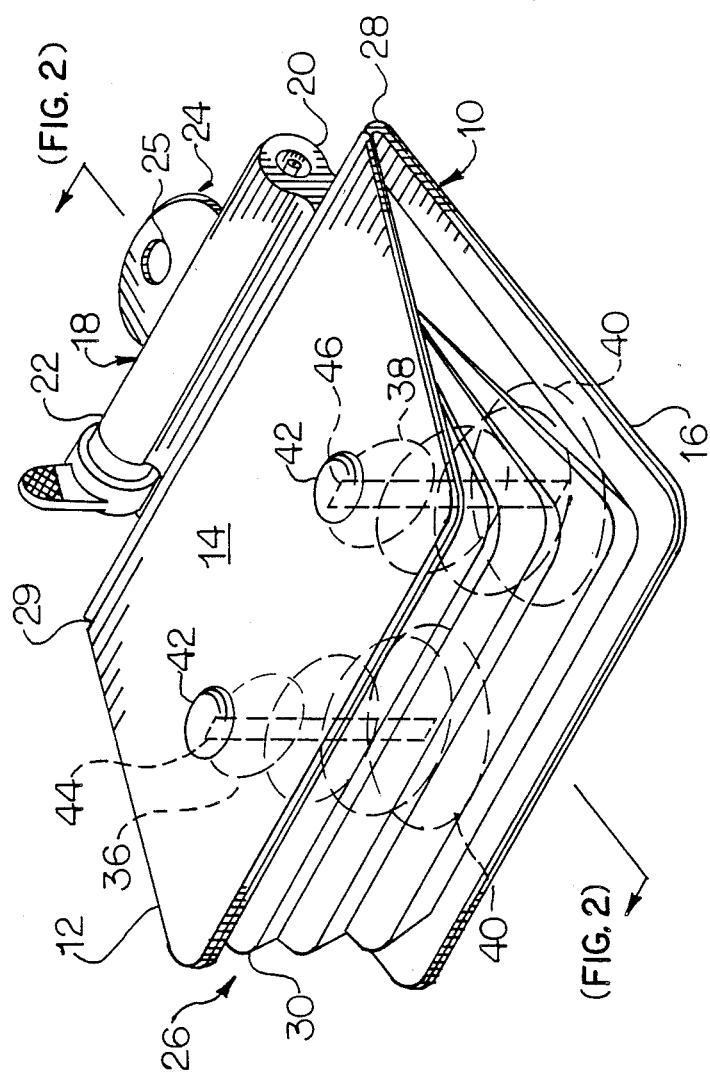
FIG. 1 is a perspective view of the body fluid drainage device herein.

The body fluid drainage device herein will be described with regard to the accompanying drawings.

FIG. 1 is a perspective view of the preferred body fluid drainage device 10. The body fluid drainage device has a generally wedge-shape that forms a reservoir housing 12 for collecting and holding body fluid drained from a patient. The reservoir housing 12 also functions when activated to create a partial vacuum to draw the body fluid from a patient.

The reservoir housing has a first sidewall 14 which is a relatively flat surface that is attached to a second sidewall 16 that also provides a relatively flat planar surface. The first and second sidewalls are joined along a common edge. The common edge can be a living hinge 28. The term "living hinge" as used herein means a reduced, mechanically oriented section which provides strength and which enables free movement of one sidewall relative to the other. If a living hinge is provided on both sidewalls, there would be freer movement of each such sidewall. With respect to FIG. 2, the living hinge 28 is formed by the recess 29 extending along the first sidewall 14.

The first and second sidewalls can have any geometric shape. The generally rectangular shape shown in the figures is advantageous as it can provide various edges on which the reservoir housing can stand otherwise unsupported.

The reservoir housing can be constructed from an integrally molded thermoplastic material. Various materials can be used to construct the housing, including high density polyethelyne. High density polyethylene is a preferred material as it provides acceptable mechanical properties and it retains living hinge integrity. High density polyethylene can be irradiated by gamma irradiation which is widely used in sterilization of medical products.

If no living hinge is provided, a prestress can be placed on the first sidewall and second sidewall so that they are joined forming a generally V-shape or wedge shape as shown in FIGS. 1 and 2. A prestress is created in the hinge joining the two sidewalls so that as the first sidewall is compressed towards the second sidewall, there is a tendency for the sidewalls to revert to their relaxed state, which is the open V-shape shown in the figures.

The reservoir housing 12 also includes an inlet and outlet housing 18. The inlet and outlet housing 18 can be a cylindrically shaped housing that is secured to the common edge of the first sidewall and second sidewall. The preferred embodiment of the inlet and outlet housing 18 can be integrally molded along with the first sidewall and second sidewall. The inlet and outlet housing 18 is a hollow cylindrical housing having a lumen extending therethrough for permitting fluid flow into and out of the reservoir housing 12. The inlet/outlet housing 18 includes an inlet port 20 on one end which can be connected to a catheter or drainage tubing. At the opposite end, the inlet and outlet housing has an outlet port 22 for draining fluid from the reservoir housing 12. A baffle can be placed in the cylinder between the inlet and outlet to provide a means for directing fluid into the reservoir. The drainage device can be provided with a hangar assembly 24. Such a hangar assembly can be an integrally molded planar surface having an aperture 25 through which the device can be secured in a hanging position.

Enclosing the reservoir housing 12, is a third sidewall 26. The third sidewall 26 is a pleated, flexible material that is sealed to the facing surfaces of the first sidewall and second sidewall to provide a fluid tight seal. The first sidewall, second sidewall and third sidewall thereby form a reservoir or chamber within the reservoir housing for receiving fluid.

The third sidewall can be constructed from any suitable flexible material, such as a flexible thermoplastic rubber material. The third sidewall is wedge-shaped and has pleats or flutes 30. The third sidewall resembles a bellows shroud, and upon activation of the housing, the third sidewall collapses with the pleats collapsing upon one another until they essentially reach a nearly solid stacked height. As the housing seeks to return to its prestress state, it creates a partial vacuum within the housing. The partial vacuum draws fluid into the reservoir thereby collecting fluid. The third sidewall then reverts back to its original configuration. Any suitable material which provides the necessary characteristics can be selected for the third sidewall. A high density polyethylene blended with a thermoplastic rubber provides such characteristics. It is desirable that the third sidewall be moldable, puncture resistant, resilient and provide some transparency. Transparency is preferred so that fluid collected in the reservoir can be viewed through the third sidewall. It is desirable to view the collected fluid to look for indications that could provide insight into the conditions of the patient. It is also desirable to be able to view the collected fluid to determine the volume of fluid that has been collected. In this regard, graduations can be provided on the housing as an indication of the volume of fluid collected. As can be seen in FIGS. 1 and 2, it is also desirable to seal the third sidewall to the inner surfaces of the first and second sidewalls so that upon collapse of the housing, the third sidewall remains within the perimeter defined by the edges of the first and second sidewalls.

As can be seen in FIGS. 1 and 2, the third sidewall is provided with two sets of pleats or flutes 30. The first set of pleats extends to a first pleat fulcrum point 32 and the second set of pleats extends to a second pleat fulcrum point 34. Providing two sets of pleats along the third sidewall reduces the bunching of material that can be present if a single set of pleats were used terminating in a pleat fulcrum point at the apex or at the living hinge. Providing a first pleat fulcrum point 32 spaced from the living hinge 28 creates an ease of operation of the body fluid drainage device.

Another reason for providing two pleat fulcrum points for the pleated third sidewall is that the crease in the third sidewall will always be present, as the sidewall never extends to a "straight wall" or taught condition between the first sidewall and second sidewall of the reservoir housing. Such a feature also provides a rigidity to the third sidewall.

The body fluid collecting device herein also includes a spring component which aids the housing after it has been collapsed to return to its uncollapsed state, whereby during its return to its uncollapsed state a partial vacuum is created within the reservoir to draw fluid into the reservoir. The spring force can be provided by interconnecting the first and second sidewalls, as well as the combination of such a feature with the resilient third sidewall. However, in the preferred embodiment, a first conical spring 36 and a second conical spring 38 are provided within the reservoir between the first and second sidewalls. The first and second conical springs store and release energy to create a preselected range of vacuum within the housing. This range can be varied by spring selection to accommodate various vacuum pressure needs. The springs can be selected to provide a predetermined preload condition within the housing. It was determined by the inventors herein that a conical spring achieves the flattest and most effective suction curve of any such spring loaded device. A conical spring enables the housing to be compressed to achieve a minimum of dead space which maximizes suction performance. These springs can be constructed of any suitable material. However, it is preferred that a corrosion resistant material be selected, as the springs will be in contact with the collected fluid. The first and second springs can be mounted in spring retaining recesses 40 and 42 on the facing surfaces of the first and second sidewalls.

Although conical coiled springs have been disclosed herein, other springs could be used. For example, leaf springs, cylindrical shaped springs and the like can also be used.

The housing can also include a pair of spring limiters 44 and 46 for the respective first and second springs. The spring limiters define the maximum opening of the housing. The limiters resist the preload force developed by the compression springs. The limiters can be constructed of any suitable material. The limiters can be secured to the facing surfaces of the first sidewall and second sidewall, or the limiters can encircle the coils of the springs (as shown in FIG. 2) to limit the extent of the springs elongation. Limiter adjustment can allow for varying volumetric and suction ranges.

As shown in FIGS. 1, 2 and 3, the housing assembly can include a cylindrically shaped conduit 50 which forms the inlet and outlet housing 18. The cylindrically shaped conduit 50 can be integrally molded from the same material forming the first and second sidewalls 14 and 16. The cylindrically shaped conduit 50 is shown in and can be described with regard to FIG. 3.

With reference to FIG. 3, the cylindrically shaped conduit 50 includes a conical projection 52 that includes an annular recess 53 to provide a mating capability for an end of a length of drainage tubing. The annular recess in the inlet port provides flex relief for the drainage tubing. The conical projection 52 includes a lumen which opens into the lumen or fluid passageway 60 of the cylindrical shaped conduit 50. An inwardly projecting conical member 58 can be provided within the cylindrical shaped conduit for mounting a one-way valve 54. A one-way valve 54 can be a miter valve as shown, or any other suitable one-way valve which will permit fluid flow into the reservoir, but which will prevent fluid from flowing from the reservoir outwardly of the inlet port 20. The miter valve 56 shown in FIG. 3 projects inwardly of the lumen 60.

The internal lumen 60 of the cylindrically shaped conduit 50 has a connecting lumen 62 that provides fluid flow communication between the cylindrically shaped conduit 50 and the reservoir defined by the first sidewall, second sidewall and third sidewall. The connecting lumen 62 can be of any convenient shape, and in the preferred embodiment is a linear slit formed between cylindrically shaped conduit and the reservoir within the reservoir housing 12.

The cylindrically shaped conduit 50 also provides the outlet port 22 through which fluid can be removed from the reservoir housing. The outlet port can include an annular recess 64 which can receive an encircling strap ring 70. The strap ring 70 can be connected to a strap 68 which holds a cap or plug 66 for capping or plugging the outlet port. The cap 66 can include a projecting plug 72 that can mate and close the outlet opening 74 to prevent fluid from flowing from the outlet port when it is undesired. The cap can include an undercut or recess which can mate with a flange on the outlet port to provide a double-lipped seal. A one-way valve 76 can be provided in the outlet port to prevent fluid from entering the reservoir through the outlet port. When a one-way valve is present, a closed system is formed while a partial vacuum is present in the reservoir.

In use, the body fluid drainage device is connected to a wound drainage catheter in a patient. The outlet port is opened to permit the expulsion of air in the reservoir. By grasping the reservoir housing with one hand (or both), the attendant or operator can squeeze the first sidewall of the reservoir housing towards the second sidewall. Such an action compresses the springs and the third sidewall. After having compressed the first sidewall towards the second sidewall, the cap 66 can be inserted into the outlet port to plug the outlet port. When a one-way valve 76 is present in the outlet port, the housing remains collapsed allowing the operator sufficient time to seal the outlet port without loss of partial vacuum.

The drainage device then seeks to recover to its original prestressed state. The first and second springs force the first sidewall away from the second sidewall. This motion creates a partial vacuum within the reservoir which draws fluid from the patient into the inlet port and into the reservoir.

The volume of fluid collected can be monitored visually through the transparent third sidewall. When the drainage device becomes filled with fluid, the fluid can be emptied by removing the plug or cap from the outlet port and pouring the collected fluid out of the reservoir. If a valve is present, a gentle squeezing of the first and second sidewalls can facilitate emptying of the fluid contents. The device can be reactivated by compressing the first sidewall toward the second sidewall and replacing the cap 66 into the outlet port.

The fluid drainage device herein provides the advantages that it can be utilized with one hand to collapse the device, thereby freeing the other hand of the attendant to close the outlet port. The overall structure of the preferred embodiment disclosed herein is also advantageous in that it provides an optimum location of the outlet port for pouring the contents from the reservoir. That is, the outlet port is on a "corner" of the device which corner can be oriented downwardly for collecting the fluid, and thereby enabling drainage of the collected fluid. The device herein provides an advantage of its one-hand operation due to its mechanical advantage when collapsing the springs. The springs are at one end of each lever arm (the first and second sidewalls) which are joined at the apex or living hinge 28. The living hinge provides an ability to collapse the first and second sidewalls substantially upon themselves which provides an increased efficiency in creating a partial vacuum, that is an increase in volumetric exchange between the inside and outside of the reservoir.

The body fluid collection device herein provides a single patient use portable device which can be manually activated, capped and connected to a properly placed drain within a patient to provide suction for removing exudate and other bodily fluids from a body cavity. The reservoir within the device is sealed to hold and measure fluid volume. The device can be disposed of when filled or emptied through a pour spout, reactivated and recapped enabling the removal of additional fluid. The inlet port is provided with a one-way reflux valve for preventing contaminated fluids collected in the reservoir from returning to the patient. The wedge shape and living hinge construction of the device facilitates holding during emptying, enables one-hand activations and provides a mechanical advantage over internal springs for lower activation forces and more consistent vacuum pressures.

We claim:

1. A body fluid drainage device comprising:

A wedge-shaped reservoir evacuator having a first sidewall and a second sidewall joined along a coextending common edge, and a third collapsible pleated sidewall extending between the nonjoined edges of the first sidewall and second sidewall to form a reservoir between the first, second and third sidewalls, the third sidewall having a collapsed position wherein the third sidewall is substantially positioned inwardly from the edges of the first sidewall and the second sidewall, wherein the third sidewall comprises a pleated sidewall with two sets of pleats extending from two apexes, the first apex being closer than the second apex to the common edge between the first sidewall and the second sidewall;

an inlet port means in fluid communication with the reservoir for introducing fluid to the reservoir;

a one-way valve means in the inlet port means for preventing fluid from flowing out of the reservoir through the inlet port means;

an outlet port means in fluid communication with the reservoir for emptying fluid from the reservoir; and biasing means in the reservoir evacuator for biasing the first sidewall and second sidewall apart, such that following compressing the first sidewall towards the second sidewall, the first sidewall and second sidewall move away from each other creating a partial vacuum within the reservoir for drawing fluid into the reservoir.

2. A body fluid drainage device as recited in claim 1 wherein the third sidewall comprises a transparent sidewall for providing viewing of fluid collected in the reservoir.

3. A body fluid drainage device as recited in claim 1 wherein the first sidewall is joined to the second sidewall forming a living hinge.

4. A body fluid drainage device as recited in claim 3 wherein the first sidewall, second sidewall and living hinge comprise an injection molded material.

5. A body fluid drainage device as recited in claim 1 further comprising a one-way valve means in the outlet port for permitting fluid to be evacuated through the outlet port.

6. A body fluid drainage device as claimed in claim 1 wherein said first sidewall is substantially flat, upon said first sidewall being placed in a substantially horizontal position, said second sidewall may be compressed towards said first sidewall.

7. A body fluid drainage device comprising:

a first sidewall having a proximal edge, a distal edge and two opposite lateral edges;

a second sidewall having a proximal edge, a distal edge, and two opposite lateral edges, said first sidewall and second sidewall being joined adjacent their respective proximal edges;

a third collapsible sidewall extending between the respective distal edges and lateral edges of said first sidewall and said second sidewall, said third sidewall having an extended position and a collapsed position, said third sidewall in the collapsed position being substantially positioned inwardly of said distal and lateral edges of said first and second sidewalls, said first, second and third sidewalls contacting the collected body fluids;

an inlet port means in fluid communication with the reservoir for introducing fluid to the reservoir;

a one-way valve means in the inlet port means for preventing fluid from flowing out of the reservoir through the inlet port means;

an outlet port means in fluid communication with the reservoir for emptying fluid from the reservoir, wherein said inlet port means and said outlet port means have longitudinal axes, which are substantially parallel to one another and to said first sidewall and said second sidewall proximal edges; and biasing means in the reservoir evacuator for biasing said first sidewall and said second sidewall apart, such that following compressing the first sidewall towards the second sidewall, the first sidewall and second sidewall move away from each other creating a partial vacuum within the reservoir for drawing fluid into the reservoir.

8. A body fluid drainage device as claimed in claim 7, wherein said inlet port longitudinal axis and said outlet port longitudinal axis are substantially coaxial.

9. A body fluid drainage device as claimed in claim 7, wherein said first sidewall and said second sidewall comprise a unitary molded component.

10. A body fluid drainage device as claimed in claim 7, wherein a unitary molded component comprises said inlet port means, said outlet port means, said first sidewall, said second sidewall, and said third sidewall.

* * * * *